United States Patent [19]

Henniger et al.

[11] 4,358,588
[45] Nov. 9, 1982

[54] PROCESS FOR PREPARING CEPHALOSPORANIC ACID COMPOUNDS

[75] Inventors: Peter W. Henniger, Leiden; Johannes K. van der Drift, Delft; Gerard J. van Veen, Pijnacker; Jagdish C. Kapur, Delft, all of Netherlands

[73] Assignee: Gist-Brocades N.V., Delft, Netherlands

[21] Appl. No.: 193,801

[22] Filed: Oct. 3, 1980

Related U.S. Application Data

[63] Continuation-in-part of Ser. No. 937,988, Aug. 30, 1978, abandoned.

[30] Foreign Application Priority Data

Aug. 11, 1978 [EP] European Pat. Off. ........ 78200140.8

[51] Int. Cl.$^3$ ........................................... C07D 501/06
[52] U.S. Cl. ..................................... 544/030; 544/26; 260/239.1; 424/246
[58] Field of Search ..................... 544/28, 30, 26, 27; 260/239.1; 424/246, 271

[56] References Cited

U.S. PATENT DOCUMENTS 3,965,098  6/1976  Robinson ............................ 424/246
4,148,817  4/1979  Wright ............................... 424/246

Primary Examiner—Nicholas S. Rizzo
Attorney, Agent, or Firm—Hammond & Littell, Weissenberger and Muserlian

[57] ABSTRACT

A process for the preparation of [D-α-amino-p-hydroxyphenylacetamido]-penicillanic acid or cephalosporanic acid compounds comprising reacting a compound having a formula selected from the group consisting of

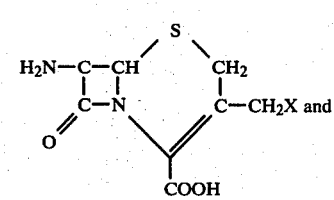

and

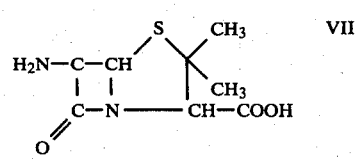

wherein X is selected from the group consisting of hydrogen, acetoxy and five-membered heterocyclic group containing at least one hetero atom of the group consisting of oxygen, sulfur and nitrogen and optionally substituted with e.g. lower alkyl, this residue being attached to the 3-CH$_2$ group via sulfur atom and wherein a NH radical if present has optionally been silylated with at least one mole equivalent of a silylating agent producing

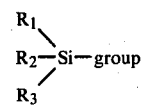

wherein R$_1$, R$_2$ and R$_3$ are individually selected from the group consisting of lower alkyl, benzyl, cycloalkyl and phenyl in an inert anhydrous, organic solvent, preferably a water-inmiscible organic main-solvent, to form a compound having a formula selected from the group consisting of

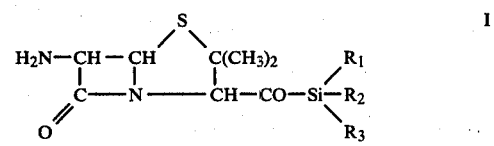

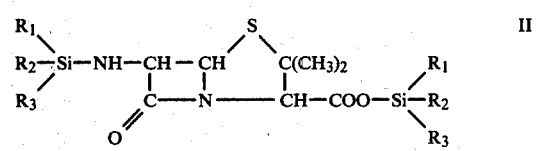

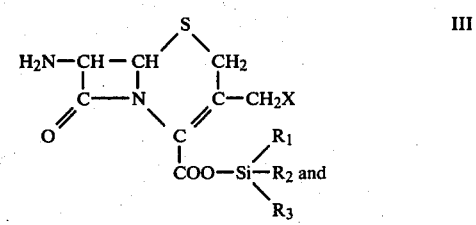

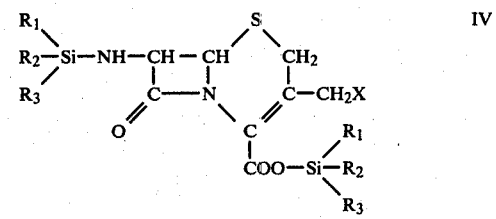

adjusting the pH to a scale value of 5.5 to 7.5 and reacting the resulting compounds in a pre-cooled solution with an at least equimolar amount of a compound of the formula

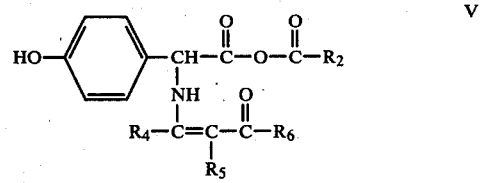

wherein R$_4$ is lower alkyl, R$_5$ is selected from the group consisting of hydrogen and lower alkyl and R$_6$ and R$_7$ are lower alkoxy.

13 Claims, No Drawings

PROCESS FOR PREPARING CEPHALOSPORANIC ACID COMPOUNDS

PRIOR APPLICATION

This application is a continuation-in-part of our co-pending, commonly assigned application Ser. No. 937,988 filed Aug. 30, 1978, now abandoned.

STATE OF THE ART

A process is generally known from British Patent No. 1,339,605 for the production of D-α-amino-p-hydroxybenzylpenicillin but according to Examples 1 to 5 thereof only in economically non-interesting yields (Example 1: 43% with a purity of 80%, Example 3: 20% with a purity of 16%, Example 4:37% with a purity of 93%, while Examples 2 and 5 only just show the presence of the above-mentioned compounds).

On the other hand, a process comprising acylation of previous silylated cephalosporanic acid derivatives of the formula III and/or IV with a mixed anhydride of formula V is generally know from e.g. published Dutch application NL 6912811, British patent No. 1,073,530 and more particularly from the British patent No. 1,460,914.

However, especially from e.g. Examples 3 and 13 of the latter patent, a skilled person cannot derive in any way that an acylation of e.g. 7-amino-3-((1H)-1,2,3-triazol-5-yl)-thiomethyl-3-cephem-4-carboxylic acid or its trimethyl-silylester, by means of e.g. ethoxycarbonyl D-α-(1-carbomethoxypropen-2-yl)-amino-p-hydroxyphenyl acetate could be carried out with economically attractive yields. More particularly in Example 13, the conversion of 0.02 mol of 7-amino-3-(1,2,3-triazole-5-yl)-thiomethyl-3-cephem-4-carboxylic acid which has previously been reacted with 0.06 mol trimethylchlorosilane in the presence of 0.06 mol of an about 2:1 mixture of triethylamine and N,N-dimethylaniline with a reaction mixture prepared in the usual way in acetonitrile from 0.05 mol of the Dane salt and ethyl chloroformate, seems to lead only to rather unattractive yields (see e.g. pages 21 line 38 in connection with with lines 5–10 of the same page).

Other patent literature relating to the preparation of this type of cephalosporanic acid derivatives showed only economically unattractive processes such as U.S. Pat. No. B 516.047, Example 1, column 7, line 44, Example 5A, line 52 and Example 6, U.S. No. 3,946,003, Example 1 (column 11, line 65) and Example 3 (column 12, line 62). Moreover, according to column 4, lines 1–5 and Example 1, (column 10), the previous silylation of the phenolic p-hydroxy group seemed inevitable for obtaining practical results which necessity otherwise also appears from Example 1 on pages 13 and 14 of the German application DT-2600880 and from the Examples 1–5 of German application DT-2626280.

Therefore, it was less attractive for the experts to develop the method described in the said British Pat. No. 1,339,605 than to look for alternative acylating methods in the search for a new and improved method for the preparation of the desired compound with an economically attractive yield and a relatively high purity. An additional modern requirement for the preparation method on a technical scale is, moreover, that the unavoidably occurring impurities are removable in a cheap and simple manner to reach the levels of purity dictated by governments.

It is known from the literature to prepare penicillanic acid and cephalosphoranic acid derivatives by acylating 6-APA or 7-AC(D)A and their derivatives with the hydrochloride of 2-phenylglycine-chloride and derivatives thereof having a substituted phenyl group, whereby the said acid choride is obtained by reacting the substituted phenylglycine with reagents like phosphorus pentachloride, thionyl chloride and phosgene. Although improved processes for the preparation of D-(—)-2-(p-hydroxyphenyl)-glycyl-chloride hydrochloride and the crystalline hemidioxane solvate thereof are known from British Pat. No. 1,466,637 and No. 1,460,915 the acylation of 6-APA or 7-A(D)CA or its 3-methyl modification with the above-mentioned acylating agent did not hitherto lead to results aimed at, mainly because either the product formed was too impure that further recovery of a product of the required quality hardly appeared to be possible, or the starting D-2-(p-hydroxyphenyl)-glycyl chloride hydrochloride of the required quality (purity) is only available for economically unattractive prices, if at all.

The occurring impurities found, if an acid chloride hydrochloride in economically necessary amounts for acceptable prices is used, appear to be in agreement with the indications about the accompanying impurities in the final products and the low yields of the rather similar acylation of the said D-(—)-2-(p-hydroxyphenyl)-glycyl chloride hydrochloride of 7-aminocephalosporanic acid derivatives of British Pat. No. 1,460,916 (viz. Examples 2, 4 and 9 especially page 17 lines 32–34 and the Example 8 referring to further purification of the desired product). German patent application Ser. No. 2,520,647 discloses in this connection on page 2, lines 10 to 20 also that the application of generally used acylating agents such as acid halides cannot be properly applied in the amoxicillin synthesis.

A process for the preparation of amoxicillintrihydrate is also known from published German patent application DT 2611286 comprising the acylation of 6-APA, which has been previously silylated, with D-(—)-2-p-hydroxyphenylglycylchloride hydrochloride and leading to yields, which seem to approach to some extent the present practical requirements.

However, in the preparation of D-(—)-2-(p-hydroxyphenyl)-glycyl chloride hydrochloride according to the British Pat. No. 1,460,915 and British Pat. No. 1,466,637, phosgene is used in a relatively difficultly manageable process in which a solid is reacted with a gas. Such a process is extremely expensive in a number of countries with very stringent safety regulations, if indeed it may be applied at all. For the same reason, the process described in British Pat. Nos. 1,268,536 and 1,341,827 disclosing the preparation of 6-isocyanatopenicillanic acid and 7-isocyanatocephalosporanic acid derivatives from esters of 6-APA or 7-ACA or its 3-methyl modifications with phosgene and its subsequent reaction to form penicillins or cephalosporins are left out of consideration for the preparation of amoxicillin and the cephalosporanic acid derivatives having the corresponding side chain in 7-position.

On the other hand, German patent application Ser. No. 2,520,647, for example, discloses a process for the preparation of-inter alia-amoxicillin, in which (i) 6-APA is contacted with an excess of a strong tertiary amine base such as triethylamine in an inert, water-insoluble organic solvent such as methylene chloride or chloroform resulting in a solution of a salt of 6-APA with the base in said solvent, (ii) the remaining strong tertiary amine base is neutralized in the solvent, such as by addition of N,N-dimethylacetamide hydrochloride.

(iii) the obtained neutralized solution is contacted with a solution of a mixed acid anhydride of a short chain alkoxyformic acid and an N-protected derivative of D-2-amino-p-hydroxyphenylacetic acid, in which the N-protecting group is acid labile in a water-insoluble, inert organic solvent at a temperature of −50° C. to +30° C., preferably −30° C. to 0° C. resulting in a solution of an N-protected amoxicillin derivative, (iv) the solution so obtained is contacted with water and a strong acid such as hydrochloride acid or p-toluenesulfonic acid at room temperature or cooled to such as 0° C. to remove the acid labile N-protecting group and (v) the thus obtained amoxicillin is isolated from the thus obtained aqueous system.

Less attractive features of this process are that the process is carried out at low concentrations, that solvents become mixed so that recovery thereof becomes more difficult, and that, when adding the dimethylacetamide hydrochloride, due to local high concentrations, 6-APA, 7-ADCA or 7-ACA sometimes crystallizes, so that a very accurate dosing scheme is required.

Furthermore, a number of patent applications and patents disclose preparation methods of α-aminoacyl-penicillanic acid derivatives by acylating 6-APA with mixed anhydrides derived from modified Dane salts of D-2-amino-(p-hydroxyphenl)-acetic acid, such as those described in German patent Applications Ser. No. 1,302,847, No. 2,020,133 and No. 2,065,879 and British Pat. No. 1,327,270 and No. 1,347,979. However, the yields resulting from the use of Dane salts appeared to be unsatisfactory as well for the purpose of the present invention, and moreover, the Dane salts appeared to be available in economically unattractive quantities, if at all available.

Dutch patent Application Ser. No. 64 01841 further discloses the protection of the carboxylic group of 6-APA, 7-ACA and other amino acids by reacting it with dihalosilane derivatives and those bi-functional silicon compounds are easier accessible than the monofunctional trialkylhalogensilanes and the application thereof should, in a number of cases, lead to improved yields, as appears, such as from British Pat. No. 1,266,544 disclosing the preparation of intermediate organosilane penicillins by reaction of 6-APA and those bi-functional silicon compounds. The organosilane derivatives are acylated into ampicillin for example, so that an expert from the contents of this patent would expect that the use of the organosilane penicillins described therein would lead to interesting yields in the preparation of amoxicillin. However, this expectation could surprisingly not be confirmed by initial experiments.

From later patent applications such as British Pat. No. 1,356,737, No. 1,404,846 and No. 1,459,999, it is known to employ trivalent phosphorus derivatives instead of the above-mentioned silicon derivatives. Disadvantages of these derivatives are certainly the cost prices being 10 to 20 times higher and the toxicity and spontaneous inflamability of the di(lower alkyl) phosphorus derivatives as indicated in Inorganic Synthesis 15 (1974) pages 191 to 193, which make, the phosphorous compounds a poor substitute.

Although it is further known from a number of patent applications such as Japanese Patent application No. 49-014687 and No. 49-048892, British patents No. 1,367,342 and No. 1,382,255 and German patent applications Ser. No. 2,460,649 and No. 2,621,618, to prepare amoxicillin from 6-APA and p-hydroxy-phenylglycine or lower alkyl esters thereof by enzymatic acylation, the processes of this type are also unsatisfactory for the deemed purpose in view of the yields obtained and/or the presence of the acylating enzyme in the amoxicillin-containing solution obtained.

OBJECTS OF THE INVENTION

It is an object of the invention to provide an improved process for the preparation of [D-α-amino-p-hydroxyphenyl-acetamido]-penicillanic acid and cephalosphoranic acid derivatives in higher yields and with reduced impurity problems.

This and other objects and advantages of the invention will become obvious from the following detailed description.

THE INVENTION

The novel process of the invention for the preparation of [D-α-amino-p-hydroxyphenyl-acetamido]-penicillanic acid and cephalosporanic acid derivatives comprises reacting a compound having a formula selected from the group consisting of

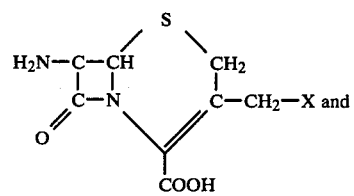

VI

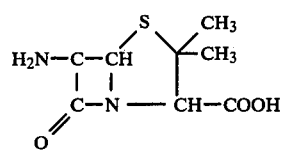

VII wherein X is selected from the group consisting of hydrogen, acetoxy and five-membered heterocyclic group containing at least one hetero atom of the group consisting of oxygen, sulfur and nitrogen and optionally substituted with e.g. lower alkyl, this residue being attached to the 3-CH₂ group via sulfur atom and wherein a NH radical if present has optionally been silylated and wherein R₁, R₂ and R₃ are individually selected from the group consisting of lower alkyl, benzyl, cycloalkyl and phenyl with at least one mole equivalent of a silylating agent producing

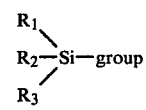

in an inert anhydrous, organic solvent, preferably a water-inmiscible organic mainsolvent, to form a compound having a formula selected from the group consisting of

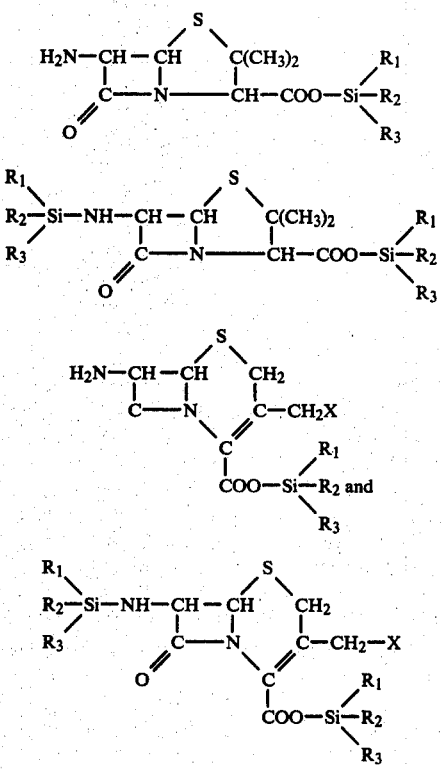

adjusting the pH to a scale value of 5.5 to 7.5 and reacting the resulting compounds in a pre-cooled solution with an at least equimolar amount of a compound of the formula

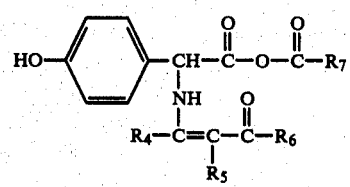

wherein $R_4$ is lower alkyl, $R_5$ is selected from the group consisting of hydrogen and lower alkyl and $R_6$ and $R_7$ are lower alkoxy. The term "lower" is intended to mean 1 to 3 carbon atoms.

The five-membered heterocyclic group as defined hereinbefore is preferably unsaturated. Suitable groups include triazol, tetrazol, thiadiazol, imidazol and 1,3,4-oxadiazol.

Examples of specific compounds which may be prepared by the said process are amoxicillin or 6-[D-α-amino-p-hydroxyphenyl-acetamido]-penicillanic acid, cefadroxil or 7-[D-α-amino-p-hydroxyphenyl-acetamido]-3-methyl-3-cephem-4-carboxylic acid, 7-[D-α-amino-p-hydroxyphenyl-acetamido]-3-acetoxymethyl-3-cephem-4-carboxylic acid and cefatrizine or 7-[D-α-amino-p-hydroxyphenylacetamido]-3-[(1H)-1,2,3-triazol-5-ylthiomethyl]-3-cephem-4-carboxylic acid and their non-toxic, pharmaceutically acceptable salts. It will be appreciated that also other rather similar cephalosporanic acid derivatives, wherein only the optionally substituted heterocyclic residue, connected via a sulfur to the 3-CH₂ group is another one such as tetrazol, thiadiazol and imidazol, but having the [D-α-amino-p-hydroxyphenyl acetamido] residue in common, may be prepared according to the novel process of the invention. In the preferred silylating agents, $R_1$, $R_2$ and $R_3$ are lower alkyl, more preferably methyl, and in the preferred compounds of formula V, $R_4$ is methyl, $R_5$ is hydrogen or methyl and $R_6$ and $R_7$ are methoxy.

Examples of suitable tertiary amines for use in preparing the acylating agent are N-methyl morpholine and N,N-dimethyl-benzylamine. The acylation reaction is preferably effected over 15 minutes to 3 hours, most preferably 1 to 2½ hours, at a temperature of −10° C. or lower, preferably −20° to −30° C. After the reaction is completed, the reaction mixture is poured into water while maintaining the pH below 2.5, preferably 0.8 to 1.2.

A suitable dry, inert organic solvent for the silylating reaction is for example acetonitrile. However, preferably an inert water-inmiscible solvent is used, e.g. methylene chloride, to which a relatively small volume of a co-solvent may be added. Suitable co-solvents are, for example, dipolar aprotic solvents such as N-methylpyrrolidon, dimethylacetamide and tetramethylurea. The silylating agent is preferably trimethylchlorosilane (TMCS) in the presence of a tertiary amine. Good results may also be obtained with trimethylsilylacetamide, bis(trimethylsilyl)-acetamide, hexamethyldisilazane and bistrimethylsilylurea.

It has been found that the way in which the silylation is carried out is very important for the final yield, and the silylation is preferably carried out in dry methylene chloride containing 2 to 3 equivalents of a tertiary amine such as triethylamine and an equivalent amount of TMCS (about 2 equivalents for amoxicillin and cefadroxil and 3 equivalents for cefatrizine), in such a way that the signal recorded by a pH electrode is adjusted at the end of the reaction at a constant value of, for example a pH scale value between 5.5 and 7.5, preferably 6.0 and 7.2, of a Radiometer pH meter type TTT2,C and a Radiometer GK 2401C electrode or an Ingold, so-called cold electrode, at a temperature between 15° and 25° C. Therefore, disilylation of e.g. of 6-APA or 7A(D-)CA is preferably carried out with practically balanced mutual amounts of tri(lower alkyl) halosilane, such as TMCS, and tertiary amine (such as TEA).

The dry, water-insoluble solvent used for the preparation of the so-called Dane anhydride may be dry methylene chloride to which dimethylformamide, sulfolane, tetrahydrofuran, N-methyl-2-pyrrolidone, 1,4-dioxane, acetonitrile, dimethylacetamide or tetramethylurea or a mixture thereof is added as a cosolvent to at most 25% by volume, or methylisobutylketone or tetrahydrofuran as main solvent to which one or more of the cosolvents mentioned above optionally may be added up to 25% by volume.

Preferably, potassium or sodium D-α-(1-carbomethoxypropen-2-yl) amino-p-hydroxyphenylacetate is reacted with, preferably, methyl chloroformate, in contrast with the opinions hitherto held as true as may be seen from Houben-Weyl, Methoden der Organischen Chemie, 4th Edition (1974) Volume XV/2, Synthese von. Peptiden, Part II, page 172. N-methylmorpholine is preferably used as a catalyst. The acid chloride is preferably added to the starting Dane salt, while the reaction is preferably carried out at a temperature of −10° C. or lower, preferably at a temperature between −10° C. and −35° C. Mixtures of methylene chloride and the indicated cosolvent with up to about 20% by volume and preferably to 10% by volume of cosolvent in the starting mixture are proposed as the optimal solvents for the preparation of the Dane mixed anhydride. Preferably, the concentrations of the cosolvent are selected so as to avoid mixing of solvents. Preferably, tetrahydrofuran, N,N-dimethylacetamide, N,N-dimethylformamide, N-methyl-2-pyrrolidone and N,N,N',N'-tetramethylurea are used as cosolvents.

According to a further preferred process, the solution of the anhydride as prepared is cooled to a temperature of −15° C. or lower and a cooled solution of silylated 6-APA, 7-ACA or methyl derivatives thereof are added rapidly with stirring as well as possible so that a temperature of −15° C. to −30° C. is reached, whereafter the reaction mixture is stirred for a further 0.5 to 3 hours. An excess of the formula V compound is preferably employed, the excess being dependent on the nature of the substituent of the 3-methyl group of the cephalosporanic nucleus. For the preparation of amoxicillin and cefadroxil a small excess is sufficient. In case of cefatrizine, having an acylatable amino group in the heterocyclic ring, at least 2 moles of the compound of formula V will be necessary.

For the preparation of amoxicillin, then, the reaction mixture is mixed with a dilute solution of an organic acid such as dilute (aqueous) hydrochloric acid solution, preferably in such a manner that the temperature becomes −50° C. to 5° C., preferably about 0° C., and the pH value becomes 1.0 to 1.5. The mixture is stirred for a further 0.5 to 2 hours at the same temperature.

According to a preferred procedure, the layers are separated. The aqueous layer containing the desired compound as its hydrochloride is washed with an inert, water-insoluble organic solvent such as methyl isobutyl-ketone or methylene chloride. The organic layer is washed with water and the wash-waters are extracted with the organic phase. Then the washing of the aqueous layer is added to the washed aqueous layer. The aqueous layer is kept at a temperature of 0° C. or lower, and the amoxicillin is recovered by crystallization in the usual way.

It will be appreciated that the initially isolated amoxicillin trihydrate may be further converted into non-toxic, pharmaceutically acceptable salts by methods known per se.

For the preparation of e.g. cefatrizine, the initially prepared compound is preferably isolated from the reaction mixture in the form of the corresponding methanolate or propylene glycolate. The solvates of cefatrizine may be converted into non-toxic, pharmaceutically acceptable salts by known methods. For the preparation of e.g. the methanolate of the cefatrizine, the initially obtained reaction mixture is mixed with methanol and then with a dilute aqueous solution of an inorganic acid such as hydrochloric acid so that finally a pH of 1.0–1.5 of the mixture was attained.

From the obtained mixture, the methanolate is prepared in the usual way such as by adjusting the pH to 1.7 to 2.4, concentration of the organic phase and addition of an inert organic solvent for a clear separation, extraction of the organic layer with ice water, concentration of the combined water layers, addition of an organic solvent such as ethyl acetate, concentration of the obtained solution, addition of methanol in large excess and adjustment of the pH to 5.5, collecting the precipitate and washing and drying. If a water inmiscible organic main solvent is used, concentration of the layers is superfluous, since the layer containing cefatrizine contains only a little water.

For the preparation of e.g. cefadroxil, this compound is preferably isolated from the initially obtained reaction mixture by mixing it with an aqueous solution of an inorganic acid so that a final pH of about 1 is attained, purification, addition of N,N-dimethylformamide in large excess, adjustment of pH to 5.5 to about 10° C., collecting of solvate crystals, washing with DMF-water mixtures and drying.

The cefadroxil may be recovered from this obtained solvate by dissolving it in water and addition of seeding crystals of cefadroxil monohydrate. However, the cefadroxil may also be more straight forwardly recovered from the initially obtained reaction mixture by the addition of seeding crystals of cefadroxil-monohydrate to the water phase obtained after the hydrolysis and purification steps.

It will be appreciated that some of the most important advantages of the acylation process of the invention are: previous and selective silylation of the p-hydroxy group is being avoided; the reaction is being carried out in a concentrated solution of the reactants; given the size of the equipment this will favorably influence the output in kilos per batch; the use of a p-hydroxyphenyl-glycol chloride hydrochloride is avoided which can only be prepared by a rather difficulty manageable process and which moreover is extremely expensive in a number of countries due to very stringent safety regulations, if indeed permission for its manufacture can be obtained at all; the use of large amounts of other additional chemicals is avoided; the desired final product can surprisingly be prepared in economically attractive initial yields in a quality acceptable under available health regulations while at the same time, the number of purification steps can be reduced with attendant smaller losses of desired compound; in most cases mixing of solvents occurs so that recovery of solvents used is rather simple and economically advantageous, while moreover the starting solvent system can be fairly easily dried; and the chance of undesired and unexpected crystallization of 6-APA, 7-ACA or its 3-methyl modifications is practically nil so that a reliable and rather trouble-free process is provided.

It will be appreciated that at least two undesired side reactions always will be considered by skilled people when acylating with a mixed anhydride. These side reactions are: (1) the undesired acylation whereby alkoxycarbonylamino penicillanic acid or cephalosporanic acid derivatives will be formed; and (2) partial racemization of the N-protected amino acid, or salt thereof into the mixed anhydride.

The avoidance of the first side reaction by rather simple means would be regarded as rather impossible by skilled people, the more so as this side reaction at least often partially has a trivial nature, relating to the fact that mixed anhydrides naturally are more or less labile and are inclined to disproportionate into two symetrical anhydrides. Hence, the preparation of the mixed anhydride as well as the conversion of this anhydride with an amino acid will be always carried out at low temperature.

The second undesired side reaction (racemization) may only be mainly avoided by trial and error methods.

While according to the literature, ethyl chloroformate and in the case of racemization when using this last mentioned reactant, in a somewhat lesser extent-isobutyl chloroformate, pivaloyl chloride and benzoyl chloride were regarded as suitable reactants, and to the contrary the use of methyl chloroformate should certainly not be recommended the use of the cheap methyl chloroformate surprisingly appeared to lead to significantly improved results.

It will be appreciated, that for the preparation of the mixed anhydride and the subsequent acylation, preferably solvent systems may be considered which will meet the requirements of economy (recovery, recycling) and of ecology.

These preferred conditions could surprisingly be fulfilled by the certainly not predictable application of the presently proposed solvent system.

The application of the solvent systems during the preparation of the mixed anhydride surprisingly appears to lead to: (a) an improved and moreover more reproduceible and reliable formation of the mixed anhydride and hence an improved conversion yield to the desired compound; (b) an improved yield of the desired compound in combination with a simultaneous increase of the concentrations to an attractive level, with reference to the present economical requirements; (c) the rather unexpected application of N,O-silylated 6-APA and 7-ACA or derivatives thereof for the reaction with the mixed anhydrides in the indicated yields; (d) to improved conversion yields in the case of the application of cosolvents of the amide type for certain conversions of silylated 7-ACA derivatives; and (e) the possibility to carry out the silylation reaction and the preparation of the mixed anhydride in one and the same water immiscible main solvent, and more particularly dichloromethane on account of which the presently required recovery of solvents is drastically simplified.

Moreover, it was found that during the preparation of the mixed anhydride, the catalysis may be performed by; N-methyl morpholine as preferred catalyst as well as other similar (cyclo) aliphatic tertiary amines known from literature for this purpose, may be used as catalysts. The presence of catalysts may be avoided by the use of significant amounts-e.g. about one third of the total solvent volume-of cosolvents of the amide type.

As in industrial processes the application of thoroughly dried solvents and/or Dane salts of very high purity is an ideal that will never be realized completely, a slight excess of the starting Dane salts and of (lower) alkyl chloroformates are preferably used. In one of the preferred embodiments of the process of the present invention, amoxicillin trihydrate is prepared, starting from dry methylene chloride, 6-aminopenicillanic acid, trimethylchloro silane in the presence of triethylamine in exactly balanced mutual amounts and in an amount of about two equivalents with reference to 6-APA, of potassium D-α-(1-carbomethoxypropen-2-yl)-amino-p-hydroxyphenylacetate with N-methylmorpholine as catalyst; and a cosolvent selected from N,N-dimethylacetamide, N-methylpyrrolidone, N,N-dimethylformamide, and tetramethylurea or mixtures thereof, and methyl chloroformate, while the solutions of the in situ prepared silylated 6-APA acid and the mixed anhydride are pre-cooled to −40° C. and the reaction is performed in two hours at a temperature of −30° C., followed by recovering amoxicillin by known methods.

In the following examples there are described several preferred embodiments to illustrate the invention. However, it should be understood that the invention is not intended to be limited to the preferred embodiments.

EXAMPLE 1

Preparation of 7-[D-α-amino-(p-hydroxyphenyl)-acetamido]-3-[(1H)-1,2,3-triazol-5-yl-thiomethyl]-3-cephem-4-carboxylic acid methanolate STEP A: O,N-silylated 7-amino-3-[(1H)-1,2,3-triazol-5-yl-thiomethyl]-3-cephem-4-carboxylic acid A suspension of 4.173 g (13.33 mmol) of 7-amino-3-[(1H)-1,2,3-triazol-5-yl-thiomethyl]-3-cephem-4-carboxylic acid, prepared by the conversion of 7-ACA with a slight excess of sodium (1H)-1,2,3-triazol-5-thiolate in water at elevated temperature and followed by recrystallization from water, in 50 ml of dry acetonitrile, purified by distillation and stored over weakly acidic aluminium oxide (water content <25 g/liter) was prepared, 5.617 ml. (40.29 mmol) of triethylamine were added to the suspension at 3°–5° C. While continuously passing nitrogen over the surface of the stirred mixture and at a temperature slightly below 5° C., 5.179 ml (40.99 mmol) of trimethyl chlorosilane were added thereto. The cooling bath was removed and stirring was continued for 20 hours at room temperature (about 20° C.) and then for 3–4 hours at about 30° C. The preparation of (O,N-silylated 7-amino-[(1H)-1,2,3-triazol-5-yl-thiomethyl]-3-cephem-4-carboxylic acid was cooled to −20° C. for Step C.

STEP B: Methoxycarbonyl D-α-(1-carbomethoxypropen-2-yl)amino-p-hydroxyphenyl-acetate 6 droplets (from a Pasteur pipette) of N-methylmorpholine were added to a stirred and cooled (0° C.) suspension of 11.478 g (37.88 mmol) of potassium D-α-[1-(carbomethoxypropen-2-yl)-2-amino]-phenylacetate in a mixture of 50 ml distilled tetrahydrofuran and 12 ml of tetramethylurea and while continuously passing nitrogen over the surface of the reaction mixture, the slurry was cooled to −10° to −12° C. Then, a solution of 3 ml (38.8 mmol) of methylchloroformate with a purity of 97% in 7 ml of distilled tetrahydrofuran was added thereto dropwise while a reaction temperature of −10° up to −12° C. was maintained. The resulting mixture was then stirred for 30 minutes at −10° to −12° C. after which mixture was subsequently cooled to −20° C.

STEP C: 7-[D-α-amino-p-hydroxyphenylacetamido]-3-[(1H)-1,2,3-triazol-5-yl-thiomethyl]-3-cephem-4-carboxylic acid-methanolate Under a nitrogen atmosphere, the mixture containing the mixed anhydride prepared in Step B was quickly added at −20° C. to the reaction mixture of Step A and the resulting mixture was then stirred for 3 hours at −20° C. and thereafter stored overnight at −18° C. with stirring, the mixture was gradually brought to 20° C. over about 45 minutes and then the mixture was filtered through a G-3 glass filter. The collected precipitate was repeatedly washed with a total of 50 ml of dry methyl isobutyl ketone after which 5 ml of absolute methanol was added thereto under ice cooling and stirring. The combined filtrate was poured into 40 ml of vigorously stirred iced water and while cooling and stirring, 4 N hydrochloric acid was added until the mixture had attained a pH of 1.5. The ice cold mixture was then stirred for 30 minutes after which the pH was raised to 2.3 by addition of triethylamine. Prior to the separation of the phases, the major part of the organic solvent was removed by evaporation under vacuo and subsequent addition of methyl isobutyl ketone until a clear two layer system was obtained. The layers were separated and the lower layer was stored in ice and the upper layer was twice extracted with 25 ml volumes of ice water. The wash waters were combined with the previously obtained lower layer and the mixture was concentrated in vacuo to a small volume at temperatures below 20° C. 150 ml of ethyl acetate were added to the residue followed by almost complete evaporation in vacuo, again at temperatures below 20° C. While maintaining the temperature below 20° C., the residual, still somewhat moist oil was dissolved in 100 ml of dry (about 99%) methanol followed by a slow introduction of triethylamine until a constant pH of 5.5 was reached. Precipitation of the desired cefatrizine methanolate started at pH 4. The mixture was additionally stirred with cooling for one hour and the precipitate recovered by filtration was washed with dry and cold methanol and dried in vacuo to obtain 4.640 g of 7-[D-α-amino-p-hydroxyphenylacetamido]-3-[(1H)-1,2,3-triazol-5-yl-thiomethyl]-3-cephem-4-carboxylic acid-methanolate. The PMR spectrum of the product indicated an exact 1:1 ratio between cefatrizine and methanol, while the crude yield of cefatrizine methanolate was 73.0%.

By careful calculation of integrals of various proton absorption signals in the PMR spectrum of a solution of the crude product in dideuterio formic acid, it was found that the hydrochloric acid salt of triethylamine was present for about 1.0% by weight and tetramethylurea for about 0.6%. Since the crude product did not contain any detectable amounts of p-hydroxyphenylglycine nor any of the starting 7-ACA-derivative, the crude product appeared to have a purity of at least 98.4% by weight. The slightly yellowish crude product could easily be converted into practically pure and stable solvates of cefatrizine such as the sesquihydrate.

EXAMPLE 2

7-[D-α-amino-(p-hydroxyphenyl)-acetamido]-3-[(1H)-1,2,3,-triazol-5-yl-thiomethyl]-3-cephem-4-carboxylic acid methanolate STEP A: Silylated 7-amino-3-[(1H)-1,2,3-triazol-5-yl-thiomethyl]-3-cephem-4-carboxylic acid 28.0 ml of triethylamine were added at −5° C. to 0° C., while continuously passing nitrogen over the surface of the mixture to a suspension of 20.865 g of 7-amino-3-[(1H)-1,2,3-triazol-5-yl-thiomethyl]-3-cephem-4-carboxylic acid in 200 ml of acetonitrile, 26.0 ml of trimethylchlorosilane were added at a temperature of 0° to 7° C. and the reaction mixture was stirred for 3 hours at about 30° C. The pH value measured with a Radiometer pH meter TTT2,C and a Radiometer GK 2401C electrode was kept constant between 6.0 and 6.5.

STEP B: Methoxycarbonyl D-α-(1-carbomethoxypropen-2-yl)amino-p-hydroxyphenylacetate 200 ml of dry tetrahydrofuran were added to 57.390 g of potassium D-α-(1-carbomethoxy-propen-2-yl)amino-p-hydroxyphenylacetate, and after cooling to 0° C., 50 ml of N,N-dimethylacetamide were added. After addition of 30 Pasteur pipette drops of N-methylmorpholine, the mixture was cooled to −10° to −15° C. and 15 ml of methyl chloroformate were added. The reaction mixture was then stirred at −10° to −15° C. for 30 minutes, whereafter the mixture was cooled to −20° C.

STEP C: Cefatrizine methanolate

Under a nitrogen atmosphere, the reaction mixture of Step B which contains the in situ prepared mixed anhydride was added at −20° C. all at once to the mixture of Step A held at −20° C. and the resulting mixture was then stirred for one hour at −20° C. and stored overnight in the refrigerator at −5° C. The mixture was brought with stirring to 20° C. over about 45 minutes and then the mixture was filtered by a G-3 glass filter. The collected material was repeatedly washed with dry methyl isobutyl ketone (about 200 ml) and the combined filtrate was cooled in an ice-bath under a nitrogen atmosphere. Subsequently 20 ml of dry methanol were added thereto and the mixture was stirred for 5 minutes. 20 ml of ice cold water were added thereto and the pH was adjusted to 1.2 with 4 N hydrochloric acid solution after which the mixture was stirred for 30 minutes with ice bath cooling. The pH was raised to 1.8 with triethylamine and the reaction mixture was concentrated to 100–150 ml by evaporation under vacuo. 150 ml of methyl isobutyl ketone were added thereto and the layers were separated. The upper layer was extracted with water (2×5 ml) and the extracts were combined with the lower layer. (If separation is difficult, a few ml of acetonitrile may be added to improve the separation.) The combined water layers were added to cold methanol so that finally a total volume of one liter was reached. By addition of triethylamine, the pH was adjusted to 5.5 and a solid precipitate was immediately formed. The mixture was then stirred for 3 hours and stored in the refrigerator overnight. The mixture was filtered, washed with 95% methanol and dried over $P_2O_5$ under vacuo at 30° C. to obtain a yield of 21.574 g (65.5%) of cefatrizine methanolate having a purity of at least 98% by weight.

EXAMPLE 3

Monohydrate of 7-[D-α-amino-(p-hydroxyphenyl)-acetamido]-3-methyl-3-cephem-4-carboxylic acid STEP A: Silylated 7-amino-3-methyl-3-cephem-4-carboxylic acid (7-ADCA).

400 ml of dichloromethane and 19.8 g (123 mmol) of hexamethyldisilazane (HMDS) were added to 35.0 g (163 mmol) of 7-ADCA and after heating to 38° C., the mixture was refluxed under a dry nitrogen atmosphere for 7.5 hours. The amount of nitrogen, which was passed over per hour, was about 20 l. (of standard conditions). The volume in the reaction flask was maintained at a constant value by addition of small amounts of dichloromethane when necessary. The 7-ADCA was completely dissolved and after the titration of the starting 1 N sulfuric acid solution in a washing bottle connected to the reaction vessel, 98% of the starting HMDS appeared to be caught as ammonia.

STEP B: D-α-(1-carbomethoxy-propen-2-yl)-amino-p-hydroxyphenylacetate 200 ml of dichloromethane were added to 58.0 g of potassium D-α-(1-carbomethoxy-propen-2-yl)-amino-p-hydroxyphenylacetamide and after cooling to −40° C., 20 ml of dimethylacetamide were added thereto while the temperature rose to −33° C. After addition of 0.5 ml of N-methylmorpholine, the mixture was cooled to −38° C. and 16.0 ml of methylchloroformate were added all at once. The temperature rose to about −30° C. and the reaction mixture was stirred at this temperature for 2 hours whereafter the mixture was cooled to −35° C.

STEP C: Dimethylformamide solvate of 7-[D-α-amino-(p-hydroxyphenyl)-acetamido]-3-methyl-3-cephem-4-carboxylic acid (cefadroxil-DMF-solvate).

The reaction mixture of Step A was cooled to −30° C. and was added as rapidly as possible to the solution of the mixed anhydride of Step B with stirring and cooling whereby a temperature of −25° C. was attained. The reaction mixture was stirred for one hour at −25° C. to −20° C. and a mixture of 200 ml of distilled water and 17 ml of conc. hydrochloric acid was added so that a temperature of 0° C. was attained. After 90 minutes stirring at 0° C., hydrolysis appeared to be completed and the pH was 1. The layers were separated and the water layer was washed with 100 ml of dichloromethane. The organic layer was washed with 50 ml of distilled water and after extraction of the washing water with the dichloromethane washings, the water layer was filtered and the filter was washed with the obtained water washings. 1500 ml of dimethylformamide were added under cooling and the pH was adjusted to 5.5 at about 10° C. by addition of 25% ammonium hydroxide solution which caused crystallization of the cefadroxil-DMF-solvate. After about one hour, the crystallization mixture was adjusted to a pH of 7 and was cooled to 0° C. After cooling for one hour at this temperature, the needle-shaped crystals were filtered, washed with 150 ml of a 90% dimethylformamide-water mixture, washed with 300 ml of ethyl acetate and dried under vacuo at about 30° C. to obtain 73.2 g (yield of 88%) of a white cefadroxil-DMF solvate. The structure was confirmed by IR and PMR spectra, showing a virtually pure product.

STEP D: Pure crystalline 7-[D-α-amino-p-hydroxyphenylacetamido]-3-methyl-3-cephem-4-carboxylic acid-monohydrate (cefadroxil-monohydrate).

The DMF-solvate of Step C was added in portions and with stirring in about 10 minutes to 175 ml of distilled water at room temperature. After the addition and dissolution of 5 g of the solvate, 1 g of seeding crystals of cefadroxil-monohydrate were added to the mixture. After the complete addition, stirring was continued for one hour and the pyramidal crystals were filtered and washed with water at 0° C. and dried under vacuo at about 30° C. to obtain 35.4 g of crystalline white cefadroxil monohydrate. The structure of the compound was confirmed by IR and PMR spectra and showed a high purity of the product. The mother liquor was evaporated to 50 ml and after addition of 600 ml of DMF, 21.3 g of the same solvate were recovered for an overall yield of 78% of cefadroxil based on the starting 7-ADCA.

EXAMPLE 4

In exactly the same way as in Example 3, Steps A to C a water layer was obtained as in Step C and this water layer was brought to crystallization without DMF, using 1 g of seeding crystals of cefadroxil-monohydrate at pH 5. 21.7 g of the desired cefadroxil monohydrate were obtained and after additional treatment of the mother liquor, an overall yield of 78.3% was attained.

EXAMPLE 5

STEP A: Silylated 7-amino-3-methyl-3-cephem-4-carboxylic acid 400 ml of dichloromethane and 45.3 ml (327 mmol) of triethylamine were added to 35.0 g of 7-ADCA (163 mmol) and 41.5 ml (327 mmol) of trimethylchlorosilane were added dropwise over a few minutes without cooling while the temperature raised to 38° C. After refluxing for one hour at 38° to 40° C. the reaction mixture was cooled to −30° C. and then 82.2 g of cefadroxil-DMF solvate were obtained by following the same additional steps B and C of Example 3 for a yield of 98.8%. The structure was confirmed by IR and PMR spectra, indicating a high purity of the obtained product. Using the same process of Step D of Example 3, the cefadroxil-DMF solvate was converted into 41.5 g of cefadroxil-monohydrate. The structure was confirmed by IR and PMR spectra which indicated a high purity of the said product. According to a Karl Fisher test, the moisture content seemed to be 5.5%. From the mother liquor, an additional 23 g of DMF solvate could be obtained for an overall yield of 89.5% of cefadroxil monohydrate based on the starting 7-ADCA.

EXAMPLE 6

STEP A: Preparation of methoxycarbonyl D-α-(1-carbomethoxypropen-2-yl)-amino-p-hydroxyphenylacetate 58 g of potassium D-α-(1-carbomethoxypropen-2-yl)-amino-p-hydroxyphenylacetate were weighed into 2 l reaction vessel and 200 ml of previously dried methylene chloride with a molecular sieve A4 were added. After cooling the mixture to −40° C. with stirring, 25 ml of tetramethylurea were added causing the temperature to rise to about −35° C. Then 0.5 ml of N-methylmorpholine and 16 ml of methyl chloroformate were added thereto. The temperature rose to about −30° C. and the reaction mixture was stirred for 2 hours at −30° C. at a pH-value of about 4. The reaction mixture was cooled to −40° C.

STEP B: Silylation of 6-APA 35 g of 6-aminopenicillanic acid were weighed into a 1 l reaction vessel and 350 ml of methylene chloride were added thereto. With stirring, 45 ml of triethylamine were added at room temperature and then 38 ml of trimethylchlorosilane (TMSC) were added over about 10 minutes while keeping the temperature at 20° to 25° C. by cooling. After stirring for 1 hour at that temperature, the pH was about 7.5. By addition of 4 ml of TMCS, the deflection on the scale of a Radiometer pH meter type TTT2,C connected to a Radiometer GK 2401C electrode was brought to pH 6±0.2.

STEP C: Preparation of 6-(D-α-amino-p-hydroxyphenylacetamido)-penicillanic acid

The reaction mixture obtained in Step B was cooled to −40° C. and was added all at once to the solution of the mixed anhydride causing the temperature to become −30° C. The reaction mixture was stirred at −30° C. to −25° C. for 1 hour and was added to 800 ml of water whereby the temperature became 0° C. and the pH became 2.5 to 3. The pH of the mixture was adjusted to 1.1 to 1.2 by addition of 18 ml of concentrated hydrochloric acid and after stirring at 0° C. for 80 minutes, the hydrolysis was complete.

The layers were separated and the aqueous layer was washed with 100 ml of methylene chloride. The organic layer was washed with 50 ml of distilled water and after extraction of the wash water with wash-methylene chloride, the wash water was added to the aqueous layer. The coupling yield was about 92% estimated on a sample. The aqueous layer was rapidly cooled to 0° C. By crystallization, the desired compound was obtained which, after filtration, was washed with 100 ml of 50% acetone-water and 100 ml of acetone and was dried in vacuo at about 30° C. to obtain about 55.5 g of amoxicillin trihydrate (82% of theoretical yield). The remaining mother liquor contains another about 10% of amoxicillin.

EXAMPLE 7

Using the same process as indicated in Example 6, except that 20 ml of dimethylacetamide were used instead of 25 ml of tetramethylurea, a coupling yield of 92% was obtained too with 55.5 g of pure amoxicillin trihydrate (82% of theoretical yield).

EXAMPLE 8

STEP A: Preparation of ethoxycarbonyl D-α-(1-carbomethoxypropen-2-yl)-amino-p-hydroxyphenylacetate A thoroughly stirred suspension of 12.97 g (42.8 mmoles) of potassium D-α-(1-carbomethoxypropen-2-yl)-amino-p-hydroxyphenylacetate in 98 ml of methylisobutylketone (distilled over $K_2CO_3$) and 33 ml of tetrahydrofuran distilled over Redal, was cooled to $-10°$ C. under an atmosphere of dry nitrogen. Then, 0.05 ml of (5 drops from a Pasteur pippette) of N-methylmorpholine were added followed by a solution of 4.2 ml (44 mmoles) of ethyl formate, previously distilled and drawn under nitrogen, in 15 ml of methylisobutylketone. The reaction mixture was stirred at the same temperature for 30 minutes and the suspension was cooled to $-20°$ C.

STEP B: Silylation of 6-APA

In a nitrogen atmosphere, 8.65 g (40 mmoles) of 6-APA were suspended in 130 ml of dry methylene chloride and 11.2 ml (80.6 mmoles) of triethylamine and 10.3 ml (82 mmoles) of trimethylchlorosilane were added subsequently. This mixture was refluxed with stirring for 1 hour and then was cooled in an ice bath to below 5° C.

Investigation of the reaction mixture by PMR spectra indicated an at least 79% conversion of the 6-aminogroup into the 6-trimethylsilyl aminogroup.

STEP C: Preparation of 6-(D-α-amino-p-hydroxyphenylacetamido)-penicillanic acid

With vigorous stirring the turbid solution of the Dane anhydride prepared in Step A and cooled to $-20°$ C. was added all at once to a cooled solution of the silylated 6-APA obtained in Step B and the mixture was stirred for a further 20 minutes in a ice bath. Then, the ice bath was removed but stirring was continued with introduction of nitrogen until room temperature was reached (about 45 minutes). The mixture was poured into with cooling 75 ml of ice water, whereafter the pH, which reached a value of 2.5 to 3 was adjusted to 1 to 1.2 with concentrated hydrochloric acid as measured with an Electrofact KCL electrode or 0.5 to 0.7 with an AgCl electrode.

After 30 minutes' stirring with ice cooling, a precipitate was not formed and, with ice cooling and stirring, a solution of 10% of KOH or NaOH was slowly added dropwise until the pH remained constant at 5.2 to 5.3 (in about 1 hour). The reaction mixture was stored in a refrigerator for 20 hours and the precipitate formed was filtered off using a G3 glass filter. The product was thoroughly washed on the filter with water followed by acetone washing. The product was dried in vacuo (generated by an oil pump, about 1 mm Hg) over a siccapent for 16 to 24 hours to obtain amoxicillin trihydrate in a yield of 71.2% with a mercurometrically measured purity of 98.4% and a biologically measured quality of 96.9%.

EXAMPLE 9

In substantially the same manner as described in Example 8, amoxicillin trihydrate was obtained in a yield of 75.6% with a mercurometrically measured purity of 98.3%, a biologically measured quality of 96% and an optical rotation $[\alpha]_{20}^D$ of $+302°$, starting from 42.8 mmoles of potassium D-α-(1-carboethoxypropen-2-yl)-amino-p-hydroxyphenylacetate in 98 ml of methylisobutylketone and 33 ml of tetrahydrofuran, 0.05 ml of N-methylmorpholine, 44 mmoles of tetrachloroformate in 15 ml of methylisobutylketone, 40 mmoles of 6-APA in 130 ml of dry methylene chloride, 80.6 mmoles of triethylamine and 82 mmoles of trimethylchlorosilane.

EXAMPLE 10

In substantially the same manner as described in Example 8, amoxicillin trihydrate was obtained in a yield of 83.5% having a purity of 96% according to hydroxylamine measurement, a biologically measured quality of 94.4% and an optical rotation $[\alpha]_{20}^D$ of $+294°$, starting from 45.6 mmoles of potassium D-α-(1-carbomethoxypropen-2-yl)-amino-p-hydroxyphenylacetate in 98 ml of methylisobutylketone and 33 ml of tetrahydrofuran, 0.05 ml of N-methylmorpholine, 46.8 mmoles of methyl chloroformate (purity 97%) in 15 ml of methylisobutylketone, 40 mmoles of 6-APA in 130 ml of dry methylene chloride, 80.6 mmoles of triethylamine and 82 mmoles of trimethylchlorosilane. The pH value measured with a Radiometer pH meter TTT 2,C and a Radiometer GK 2401C electrode was kept constant at 6.4 at the end of the silylation reaction.

EXAMPLE 11

In substantially the same manner as described in Example 8, amoxicillin trihydrate was obtained in a yield of 79.3% having a purity of 97.6% according to hydroxylamine measurement, a biologically measured quality of 95.4% and an optical rotation $[\alpha]_{20}^D$ of $+300°$, starting from 45.6 mmoles of potassium D-α-(1-carbomethoxypropen-2-yl)-amino-p-hydroxy phenylacetate in 110 ml of methyl isobutylketone and 10 ml of N-methylpyrrolidone, 0.05 ml of N-methylmorpholine, 46.8 mmoles of methyl chloroformate (purity of 97%) in 15 ml of methylisobutylketone, 40 mmoles of 6-APA in 130 ml of dry methylene chloroform, 80.6 mmoles of triethylamine and 82 mmoles of trimethylchlorosilane. The pH value measured with a Radiometer pH meter type TTT2.C and a Radiometer GK 2401C electrode was adjusted at 6.7 at the end of the silylation reaction.

EXAMPLE 12

In substantially the same manner as described in Example 8, amoxicillin trihydrate was obtained in a yield of 75% having a mercurometrically measured purity of 97.5% and a biologically measured quality of 96.5%, starting from 42.8 mmoles of sodium D-α-(1-carbomethoxypropen-2-yl)-amino-p-hydroxyphenylacetate in 195 ml of methylisobutylketone and 65 ml of tetrahydrofuran, 0.05 ml of N-methylmorpholine, 44 mmoles of ethyl chloroformate in 30 ml of methyl isobutylketone, 40 mmoles of 6-APA in 260 ml of dry methylene chloride, 80.6 mmoles of triethylamine and 82 mmoles of trimethylchlorosilane.

EXAMPLE 13

STEP A: Preparation of methoxycarbonyl D-α-(1-carbomethoxy-propen-2-yl)-amino-p-hydroxyphenylacetate 58 g of potassium D-α-(1-carbomethoxypropen-2-yl)-amino-p-hydroxyphenylacetate were weighed into 2 l reaction vessel and 400 ml of dry methylisobutylketone were added thereto. After cooling with stirring to −15° C., 0.5 ml of N-methylmorpholine and 16 ml of methyl chloroformate were added. The reaction mixture was stirred at −11° C. for 1.5 hours to form methoxycarbonyl D-α-(1-carbomethoxy-propen-2-yl)-amino-p-hydroxyphenylacetate and was then cooled to to −43° C.

STEP B: Silylation of 6-APA 35 g of 6-aminopenicillanic acid were weighed into a 1 l reaction vessel and 400 ml of methylene chloride were added thereto. After addition of 73 g of bis(trimethylsilyl)-urea, the mixture was refluxed for about 2.5 hours and the mixture was then cooled to 20° C. The "pH" reading, on the scale of a Radiometer pH meter type TTT 2C, connected with a Radiometer GK-2401C electrode, was 6.3.

STEP C:

After cooling, the mixture obtained in Step B was added as quickly as possible to the cooled solution of the mixed anhydride so that a temperature of −30° C. is reached. The reaction mixture was stirred at −30° to −25° C. for 1 hour and was added to 800 ml of water so that the temperature became 0° C. and the pH value became 2.5 to 3. The recovery was carried out in the same manner as described in Example 6 to obtain 48.4 g of amoxicillin trihydrate having a biologically measured quality of 96.8% (71.3% of theoretical yield). The remaining mother liquor appeared to contain a further 10% of amoxicillin.

EXAMPLE 14

In the same manner as described in Example 13, 48.3 g of amoxicillin trihydrate having a purity of 97.7% were obtained by reaction of methoxycarbonyl D-α-(1-carbomethoxypropen-2-yl)-amino-p-hydroxyphenylacetate and 35 g of 6-aminopenicillanic acid, previously silylated with 72.5 g of bis(trimethylsilyl) acetamide instead of the bis(trimethylsilyl)urea.

EXAMPLE 15

(a) Preparation of methoxycarbonyl D-α(1-carbomethoxypropen-2-yl)-amino-p-hydroxyphenylacetate A thoroughly stirred suspension of 58 g of potassium D-α-(1-carbomethoxypropen-2-yl)amino-p-hydroxyphenylacetate in 400 ml of dry methyl isobutyl ketone (distilled over $K_2CO_3$) is cooled to −17° C. under an atmosphere of dry nitrogen. Then 0.5 ml of N-methylmorpholine are added, followed by 16 ml of methylchloroformate. The temperature rises to −12° C. and the reaction mixture is stirred at −12° C. for 1.5 hours. The "pH" on the scale of a Radiometer pH meter, type TTT2C, connected with a Radiometer GK-2401 C electrode, finally reads 3.7. The reaction mixture is cooled to −40° C.

(b) Silylation of 6-APA 35 g of 6-APA are added to 400 ml of methylene chloride. After addition of 43 ml of triethylamine at ambient temperature and under stirring, 35 ml of trimethylchlorosilane are added in about 10 minutes at a temperature of 20°–25° C. After additional stirring for 1 hour the "pH" value is adjusted to a final value of 6.7 by the addition of 4.9 ml of trimethylchlorosilan. The mixture is cooled to −40° C.

(c) The cooled solution as obtained under (b) is added as quick as possible to the cooled solution of the mixed anhydride as prepared under (a), while the temperature rises to −30° C. The reaction mixture is stirred at −30° C. for 1 hour and is subsequently added to 800 ml of water and 25 ml concentrated (36%) HCl solution, the temperature of which is 10° C. After additional stirring at 0° C. the layers are separated and the aqueous layer is washed with 100 ml of methylene chloride. The oranic layer is washed with 50 ml of distilled water and after extraction of the washing water with the wash methylene chloride the water layers are combined.

The acylation yields appears to be about 89% according to a microbiological test on a sample. The aqueous layer is rapidly cooled to 0° C. and a final pH of 5.2 is reached. The crystallied desired compound is washed with 100 ml of an acetone-water (1/1) mixture and 100 ml of acetone, and dried under vacuo at about 30° C.

The yield is 54.0 g of amoxicillin trihydrate having a mercurometrically measured purity of 98.7% and a purity of 99.8% measured by means of the hydroxylamine method, and an optical rotation $[\alpha]_{20}^D$ of +300 based on dry matter. Yield is 80% of the theoretical yield.

The remaining mother liquor contains a further amount of 6–7% of amoxicillin.

EXAMPLE 16

In the same manner as described in Examples 13–15, 55.3 g of amoxicillin trihydrate are obtained in a yield of 81.5% having a purity of 99.8% according to a hydroxylamine method measurement, a biologically measured purity of 95% a mercurometrically measured purity of 98.6%, and an optical rotation $[\alpha]_{20}^D$ of +300, starting from 58 g of potassium D-α-(1-carbomethoxypropen-2-yl)-amino-p-hydroxyphenylacetate in 200 ml of methylenechloride and 20 ml of N-methylpyrrolidone, 0.5 ml of N-methylmorpholine, 16 ml of methylchloroformate, 35 g of 6-APA in 200 ml of methylenechloride, 43 ml of triethylamine and 35 ml of trimethylchlorosilane. The "pH" value measured with a Radiometer pH meter TTT2C, and a Radiometer GK 2401C electrode was adjusted at 6.7 at the end of the silylation reaction, while the solution of the mixed anhydride as well as the solution of silylated 6-APA were both previously cooled to −40° C. and reacted at −30° C. for 2 hours (detected acylation yield 93.1%)

EXAMPLE 17

In the same manner as described in Examples 13–15, 56.1 g of amoxicillin trihydrate are obtained in a yield of 82.7% having a purity of 99.7% according to a hydroxylamine method measurement, a biologically measured purity of 95%, a mercurometrically measured purity of 98.7% and an optical rotation $[\alpha]_{20}^D$ of +300, starting from 58 g of potassium D-α-(1-carbomethoxypropen-2-yl)-amino-p-hydroxyphenylacetate in 200 ml of methylenechloride and 20 ml of N,N-dimethylacetamide, 0.5 ml of N-methylmorpholine, 16 ml of methylchloroformate, 35 g of 6-APA in 200 ml of methylenechloride, 43 ml of triethylamine and 35 ml of trimethylchlorosilane. The "pH" value measured with a Radiometer pH meter TTT2C, and a Radiometer GK 2401C electrode was adjusted at 6.7 at the end of the silylation reaction, while the solutions of the mixed anhydride and of silylated 6-APA were pre-cooled to −40° C. and reacted at −30° C. for 2 hours (detected acylation yield 95%).

EXAMPLE 18

In the same manner as described in examples 13–15, amoxicillin was prepared in a 80% acylation yield starting from 58.0 g of potassium D-α-(1-carbomethoxypropen-2-yl)-amino-p-hydroxyphenylacetate in 400 ml of methylenechloride, 20 ml of N,N-dimethylformamide 0.5 ml of N-methylmorpholine, 16 ml of methylchloroformate, 35 g of 6-APA in 200 ml of methylenechloride, 43 ml of triethylamine and 35 ml of trimethylchlorosilane. The "pH" value measured with the same equipment as in the preceeding examples was adjusted at 6.7 at the end of the silylation reaction, while solutions of the mixed anhydride and of silylated 6-APA were pre-cooled to −40° C. and reacted at −30° C. for 2 hours.

The amoxicillin prepared by the described process was for example characterized by the following analysis data:

| | |
|---|---|
| content measured by the hydroxylamine method (based on dry matter content) | 99.8% |
| content measured mercurometrically (based on dry matter content) | 98.7% |
| volatile components | 12.6% | gas-chromatographically measured contains:

| | |
|---|---|
| acetone | 15 mg/kg |
| methylene chloride | 119.5 mg/kg |
| methyl isobutylketone | 90 mg/kg |
| dimethylaniline | 2 mg/kg |
| $[\alpha]_{20}^{D}$ (on dry matter) | 301° |
| pH value | 5.0 |
| bulk density 6 taps: | 216 ml/100 g |
| 50 taps: | 204 ml/100 g |
| heavy metals | <10 ppm |
| sulfate ash | <0.1% |
| germn number | <10/g |
| decomposition products: penicilloinic acid | 0.4% |
| penilloinic acid | 0.6% |
| solubility (clarity) HCl: | 0.6 EBC |
| NH₄OH: | 0.5 EBC |

Various modification of the process of the invention may be made without departing from the spirit or scope thereof and it is to be understood that the invention is intended to be limited only as defined in the appended claims.

EXAMPLE 19

Using the procedure of Example 5, 400 ml of dichloromethane and 35.0 g (163 mmol) of 7-ADCA were reacted with varying amounts of trimethylchlorosilane and triethylamine while controlling the pH of the reaction mixture and the yields and purity were carefully determined by the procedure of Example 5.

In experiments wherein the final amount of triethylamine or the final amount of trimethylchlorosilane exceeds 2 equivalent or 327 mmol, the extra amount above 2 equivalents were added after completion of the silylation and under control with the pH meter. In experiments wherein less than 2 equivalents of either triethylamine or of trimethylchlorosilane were employed, these deviations were of course introduced at the start of the silylation reaction.

The results are represented in the following Table.

TABLE

| Test No. | Triethylamine ml | Triethylamine mml | Trimethylchlorsilane ml | Trimethylchlorsilane mml | pH | % in DMF solvents of Cefadroxil | % in DMF solvents of 7-ADCA | % in DMF solvents of DMF | % of Cefadroxil |
|---|---|---|---|---|---|---|---|---|---|
| 1 | 45.3 | 327 | 25 | 274 | 8.1 | 65.2 | 8.5 | 26.2 | 52.5 |
| 2 | 49.3 | 356 | 41.5 | 327 | 7.7 | 66.2 | 7.2 | 26.6 | 74.1 |
| 3 | 45.3 | 327 | 41.5 | 327 | 6.5 | 70.4 | 1.3 | 28.3 | 95.4 |
| 4 | 45.3 | 327 | 41.5 | 327 | 6.0 | 71.2 | — | 28.8 | 98.8 |
| 5 | 38.5 | 278 | 41.5 | 327 | 5.35 | 62.2 | 12.7 | 25.0 | 74.0 |

EXAMPLE 20

Preparation of 7-[(D-α-amino-(p-hydroxyphenyl)-acetamido]-3[(1H)-1,2,3-triazol-5-yl-thiomethyl]-3-cephem-4-carboxylic acid methanolate.

Step A: O,N-silylated 7-amino-3-[(1H)-1,2,3-triazol-5-yl-thiomethyl]-3-cephem-4-carboxylic acid.

To a suspension of 8.346 g. (26.66 mmol) of 7-amino-3[(1H)-1,2,3-triazol-5-yl-thiomethyl]-3-cephem-4-carboxylic acid of about 90% purity, prepared by the conversion of 7-ACA with a slight excess of sodium (1H)-1,2,3-triazol-5-thiolate, in 100 ml of dichloromethane was added 11.2 ml (80.35 mmol) of triethylamine at 0°–5° C. While continuously passing nitrogen over the surface of the stirred mixture and at a temperature slightly below 5° C., 10.4 ml (82,33 mmol) of trimethylchlorosilane were added. The cooling bath was removed and the contents were gently refluxed for 90 min. The resulting product O,N-silylated product, 7-amino-3-[(1H)-1,2,3-triazol-5-yl-thiomethyl]-3-cephem-4-carboxylic acid substituted by at least more than two trimethylsilyl groups has a pH scale value of 6.5 when measured by Radiometer pH meter 28, and using a Radiometer electrode Ingold HA-401. It was further cooled to −30° C. for step C.

Step B: Methoxycarbonyl D-α-(1-carbomethoxypropen-2-yl-amino-p-hydroxyphenyl acetate.

75 ml of dichloromethane were added to 22.956 g. of potassium D-α-(1-carbomethoxy-propen-2-yl)-amino-p-hydroxyphenylacetate and after cooling to 0° to −5° C. 14 ml of N-methyl pyrrolidinone and 0.07 ml of N-methyl morpholine were added. The mixture was cooled to −38° C. and 6.1 ml of methylchloroformate were added at once. The contents were stirred for 90 min. at −30° to −35° C.

Step C: Cefatrizine methanolate.

Under a nitrogen atmosphere the reaction mixture of Step A at −30° C. was added at once to the mixture of Step B held at −30° C. and the resulting mixture was stirred for one hour at −30° C. to −35° C. and subsequently for another hour removed and stirring was continued till the temperature reached to 15° C. The mixture was filtered and the residue washed with dichloromethane. The combined filtrate was cooled in an ice-water bath and treated with 8 ml of methanol. While cooling 5 ml of 4 N hydrochloric acid and 10 ml of water were added, then with efficient stirring the pH of the reaction mixture was brought to 1.2 with 4 N HCl and stirring was continued for 30 min. Then the upper layer was separated and the lower layer extracted with 5 ml of water.

The combined extracts (upper layer + extracted layer) were combined and by adding cold methanol, the total volume was brought to 200 ml. This methanolic solution containing cefatrizine was added slowly to methanol, kept at a constant pH 5.1 by automatic addition of 10% triethylamine in methanol. The mixture was further stirred for one hour and then kept overnight at about −15° C. The crystalline precipitate was filtered, washed with 95% methanol and 99% methanol, respectively and dried in vacuo to constant weight. The yield was 8.408 g. of 7-[D-α-amino-p-hydroxyphenylacetamido]-3-[(1H)-1,2,3-triazol-5-yl-thiomethyl]-3-cephem-4-carboxylic acid-methanolate. The PMR spectrum of the product indicated an exact 1:1 ratio between cefatrizine and methanol, while crude yield of cefatrizine methanolate was 63.83%.

By careful calculation of integrals of various proton absorption signals in the PMR spectrum of a solution of the crude product in dideuterio formic acid, it was found that the hydrochloric acid salt of triethylamine was present for about 0.84% by weight. Not taking into consideration the impurity of the starting material, the yield of actually present cefatrizine was 63%. Since the crude product did not contain any detectable amount of p-hydroxyphenyl glucine nor any of the starting 7-ACA derivative, this product could easily be converted into practically pure and stable solvated of cefatrizine such as the sesqui hydrate.

EXAMPLE 21

7-[D-α-amino-(p-hydroxyphenyl)-acetamido]-3-[(1H)-1,2,3-triazol-5-yl-thiomethyl]-3-cephem-4-carboxylic acid-methanolate.

Step A: Silylated 7-amino-3-[(1H)-1,2,3-triazol-5-yl-thiomethyl]-3-cephem-4-carboxylic acid-methanolate.

To a suspension of 8.346 g. of 7-amino-3-[(1H)-1,2,3-triazol-5-yl-thiomethyl]-3-cephem-4-carboxylic acid in 100 ml of dichloromethane 11.2 ml of triethylamine were added at a temperature between 0° and −5° C., while continuously passing nitrogen over the surface of the mixture. Trimethylchlorosilane (10.4 ml) were added at a temperature of 0°–5° C. and the reaction mixture was refluxed for 90 minutes. The "pH" value when measured with a Radiometer pH meter 28 was 7.0.

Step B: Methoxycarbonyl D-α-(1-carbomethoxypropen-2-yl)-amino-p-hydroxyphenylacetate.

75 ml of dichloromethane were added to 22.956 g. of potassium D-α-(1-carbomethoxy-propen-2-yl)-amino-p-hydroxyphenylacetate, and after cooling to −10° C., 14 ml of 1,1,3,3,-tetramethylurea were introduced. After addition of 0.07 ml of N-methylmorpholine, the mixture was cooled to −38° C. and 6.1 ml of methylchloroformate were added. The reaction mixture was then stirred for 90 min. at a temperature of −28° to −35° C. Whereafter the mixture was cooled to −30° C.

Step C: 7-[D-α-amino-p-hydroxyphenylacetamido]-3-[(1H)-1,2,3-triazol-S-yl-thiomethyl]-3-cephem-4-carboxylic acid-methanolate.

Under a nitrogen atmosphere the mixture containing the mixed anhydride, prepared in situ in Step B was quickly added at −30° C. The resulting reaction mixture was then stirred for one hour at −30° C. and for another hour at −20° C. and then left overnight at −15° C. Thereafter, with stirring, the reaction mixture was brought to room temperature, filtered and the residue washed with dichloromethane. While cooling in an ice-water bath to the combined filtrate 8 ml of methanol were added, whereupon stirring was continued for 10 min. Then with stirring and cooling 15 ml of water were added, and the pH of the resulting mixture was brought to 1,2 by adding 4 N hydrochloric acid. While maintaining pH at 1,2 the mixture was stirred for 30 min. The lower layer was separated and discarded. While maintaining the temperature below 20° C., the thick oily upper layer was dissolved in 200 of dry methanol followed by a slow introduction of triethylamine until a constant pH of 5.1 was reached. The mixture was additionally stirred for 2 hours, whereupon the resulting precipitate was collected by filtration. Washing occurred subsequently with 95% and 99% methanol, and the product was dried in vacuo to constant weight. The title compound was provided in a yield of 62.4% after making corrections for the presence of a small amount of triethylamine hydrochloride.

EXAMPLE 22

7-[D-α-amino-(p-hydroxyphenyl)-acetamido]-3[(1H)-1,2,3-triazol-5-yl-thiomethyl]-3-cephem-4-carboxylic acid methanolate.

Step A: O,N-silylated 7-amino-3-[(1H)-1,2,3-triazol-5-yl-thiomethyl]-3-cephem-4-carboxylic acid.

To a suspension of crude 8.346 g (26.66 mmol) of 7-amino-3-[(1H)-1,2,3-triazol-5-yl-thiomethyl]-3-cephem-4-carboxylic acid, prepared by the conversion of 7 ACA with a slight excess of sodium (1H)-1,2,3-triazol-5-thiolate in 100 ml of dichloromethane was added 10.9 ml of triethylamine at 0°–5° C. While continuously passing nitrogen over the surface of the stirred mixture and at a temperature slightly below 5° C., 10.4 ml of trimethylchlorosilane were added. The reaction mixture was brought to 20° C. and the "pH" measured with a Radiometer pH meter 28 was 4.9. The "pH" was brought to 6.6 by adding triethylamine. The reaction mixture was then gently refluxed for 90 min. The preparation of O,N-silylated 7-amino-3-[(1H)-1,2,3-triazol-5-yl-thiomethyl]-3-cephem-4-carboxylic acid gave a pH scale value of 6.2. Finally the pH was brought from 6.2 to 7.2 with ethylamine.

Step B and Step C were performed exactly as in Example 20. The calculated yield of the dried product 75% (from NMR).

We claim:

1. A process for the preparation of [D-α-amino-p-hydroxyphenylacetamido]-cephalosporanic acid compound comprising reacting a compound having the formula

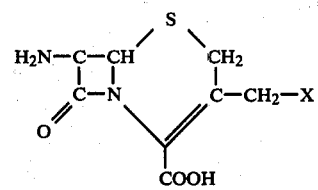

wherein X is selected from the group consisting of hydrogen, acetoxy and five-membered heterocyclic group containing least one hetero atom of the group consisting of oxygen, sulfur and nitrogen and optionally substituted with lower alkyl, the residue being attached to the 3-CH$_2$ group via sulfur atom and wherein a NH radical if present has optionally been silylated with at least one mole equivalent of a silylating agent producing

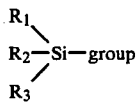

wherein R$_1$, R$_2$ and R$_3$ are individually selected from the group consisting of lower alkyl, benzyl, cycloalkyl and phenyl in an inert anhydrous, organic solvent to form a compound having a formula selected from the group consisting of

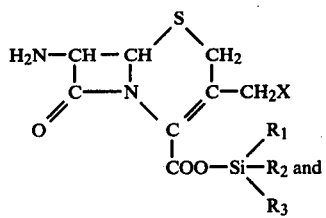

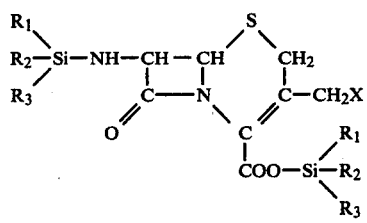

adjusting the pH to a scale value of 5.5 to 7.5 and reacting the resulting compound in a pre-cooled solution with an at least equimolar amount of a compound of the formula

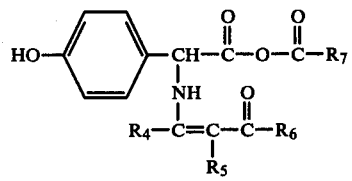

wherein R$_4$ is lower alkyl, R$_5$ is selected from the group consisting of hydrogen and lower alkyl and R$_6$ and R$_7$ are lower alkoxy, in an inert, water-insoluble organic solvent.

2. The process of claim 1 wherein at least two equivalents with respect to the 7-aminocephalosporanic acid derivative of a

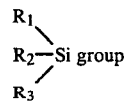

producing silylating agent, are used in dry methylene chloride.

3. The process of claim 1 wherein the starting mixed anhydride was previously prepared from the corresponding Dane salt and an acid chloride under anhydrous conditions in the presence of a tertiary amine catalyst and in a dry, inert, water insoluble, organic solvent.

4. The process of claim 3 wherein the tertiary amine is methyl-morpholine or N,N-dimethyl-benzylamine.

5. The process of claim 2 wherein the silylating reaction is carried out with trimethylchlorosilane in the presence of a tertiary amine in exactly balanced amounts.

6. The process of claim 3 wherein the dry, water-insoluble solvent for the preparation of the Dane mixed anhydride is dry methylene chloride to which a member of the group consisting of dimethylformamide, sulfolane, tetrahydrofuran, N-methylpyrrolidone, 1,4-dioxane, acetonitrile, dimethylacetamide and tetramethylurea or a mixture thereof has been added as a consolvant, or is methyl isobutylketone or tetrahydrofuran to which one or more of the said cosolvants optionally may be added.

7. The process of claim 6 wherein the solvent is dry methylene chloride to which a member of the group consisting of dimethylformamide, sulfolane, tetrahydrofuran, N-methylpyrrolidone, 1,4-dioxane, acetonitrile, dimethylacetamide and tetramethylurea or a mixture thereof is added in an amount up to 25% by volume.

8. The process of claim 6 wherein that the said cosolvent is added in an amount of at most 10% by volume.

9. The process of claim 3 wherein the preparation of the Dane mixed anhydride is carried out at a temperature of −10° C. to −35° C.

10. The process of claim 3 wherein sodium or potassium D-α-(1-carbomethoxypropen-2-yl)-amino-p-hydroxyphenylacetate is reacted with methyl chloroformate.

11. The process of claim 1 wherein R$_1$, R$_2$ and R$_3$ are lower alkyl.

12. The process of claim 11 wherein R$_1$, R$_2$ and R$_3$ are methyl, R$_4$ is methyl, R$_5$ is selected from the group consisting of hydrogen and methyl and R$_6$ and R$_7$ are methoxy.

13. The process of claim 1 wherein 7-aminodesacetoxycephalosporanic acid is reacted with about 2 molar equivalents of trimethylsilyl chloride in anhydrous methylene chloride in in the presence of triethylamine and reacting the resulting solution at −30° to 35° C. with a mixed anhydride formed by reaction of methyl chloroformate and potassium D-α-(1-carbomethoxypropen-2-yl)-amino-p-hydroxyacetate in methylene chloride and a co-solvent selected from the group consisting of N,N-dimethylacetamide, N-methyl-pyrrolidone, N,N-dimethylformamide and tetramethylurea to form cefadroxil.

* * * * *